United States Patent [19]

Scherrer et al.

[11] 4,414,156
[45] Nov. 8, 1983

[54] PROCESS FOR PRODUCING 2-METHOXYBENZANTHRONES

[75] Inventors: Walter Scherrer, Basel; Robert Portmann, Pratteln, both of Switzerland

[73] Assignee: Ciba-Geigy AG, Basel, Switzerland

[21] Appl. No.: 310,577

[22] Filed: Oct. 9, 1981

[30] Foreign Application Priority Data

Oct. 29, 1980 [CH] Switzerland ............................ 8048/80

[51] Int. Cl.³ .............................................. C07C 50/22
[52] U.S. Cl. ..................................... 260/352; 260/364
[58] Field of Search ................... 260/352, 364, 141 P, 260/141 F, 141 PR

[56] References Cited

U.S. PATENT DOCUMENTS 4,036,859 7/1977 Ribaldone et al. ................... 260/364
4,296,043 10/1981 Schroeder ........................... 260/352

Primary Examiner—Delbert E. Gantz
Assistant Examiner—Raymond Covington
Attorney, Agent, or Firm—Joseph G. Kolodny

[57] ABSTRACT

The invention relates to a novel process for producing 2-methoxybenzanthrones, starting with 1-aminoanthraquinones, which process is characterized in that, by application of a special reaction medium, namely a dimethylalkanephosphonate, which at the same time acts as a methylation agent in one of the reaction steps, the reaction is performed from beginning to end according to the principle of the single-vessel reaction, that is to say, without isolation of intermediates.

The 2-methoxybenzanthrones obtained by this process are important intermediate products for vat dyes.

11 Claims, No Drawings

PROCESS FOR PRODUCING 2-METHOXYBENZANTHRONES

The present invention relates to a novel process for producing 2-methoxybenzanthrones in a single-vessel reaction, wherein there is obtained, starting with 1-aminoanthraquinone or derivatives thereof, by way of the anthraquinone-1-diazonium salt and the reaction product thereof with a propene derivative according to Meerwein, and subsequently by way of cyclisation and finally methylation of this product, the corresponding 2-methoxybenzanthrone. The sequence of reaction is carried out, commencing with the 1-aminoanthraquinone or the diazotisation product thereof, without isolation of intermediates, in a dimethylalkanephosphonate, which serves simultaneously as reaction medium and methylation reagent.

The 2-methoxybenzanthrones obtainable by the process according to the invention are valuable intermediates for the production of dyes and pigments.

2-Methoxybenzanthrone is for example an important intermediate for vat dyes. Thus, the 5-hour alkali melt of 2-methoxybenzanthrone with potassium hydroxide and sodium methylate in polyethylene glycol 400 as solvent at 130°–135° C. under nitrogen, subsequent oxidation with atmospheric oxygen, and customary further processing, yield, in a high degree of purity, the vat dye of the formula:

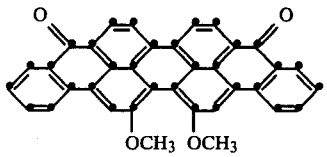

Compared with the known process, which is described for example in J. Chem. Soc. 1948, pp. 1088–9, the novel single-vessel process of the present invention is quite simple to perform and is an advance in the art.

The known process starting with benzanthrone embraces a large number of reaction steps, which usually moreover have to be isolated, namely: nitration, reduction and acetylation, through which is obtained 3-acetamidobenzanthrone, which is firstly substituted in the undesired 3-position, and from which there is produced, by nitration and hydrolysis, 2-nitro-3-aminobenzanthrone, which is subsequently converted, by diazotisation and reduction, into the desired 2-hydroxybenzanthrone, and this is then methylated to obtain 2-methoxybenzanthrone. It is obvious, in view of the large number of 8 reaction steps, apart from the considerable amount of by-products and waste products occurring, that the reaction yield is correspondingly low.

It was the object of the present invention to provide a novel process for producing 2-methoxybenzanthrone and substitution products thereof, which process would not have the aforementioned disadvantages. It has now been found that with the use of dimethylalkanephosphonate as reaction medium, which at the same time also acts as the methylation agent, it is surprisingly possible to produce, in a simple manner, in good yields and with a high degree of purity, 2-methoxybenzanthrone without isolation of the intermediates.

The invention thus relates to a process for producing a 2-methoxybenzanthrone, starting with 1-aminoanthraquinone of the formula I

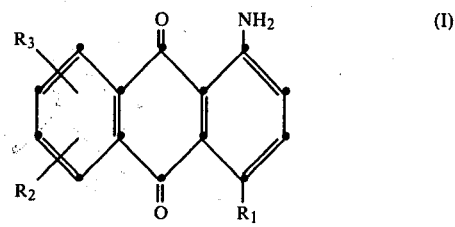

wherein $R_1$, $R_2$ and $R_3$ independently of one another are each hydrogen or chlorine, or the hydroxyl, methoxy or benzamido group, in a dimethylalkanephosphonate as the reaction medium, which at the same time acts as a methylation reagent. The unsubstituted or substituted 1-aminoanthraquinone of the formula I is firstly diazotised, and the diazonium salt is reacted, in a Meerwein reaction, with a propene derivative of the formula

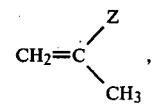

wherein Z is an electron-attracting substituent. The reaction product is cyclised by reaction with a base to give 2-hydroxybenzanthrone, and the hydroxyl group is methylated in the final reaction step.

The novel process is characterised by the fact that the reaction sequence, commencing with 1-aminoanthraquinone of the formula I or a diazotisation product thereof, is carried out in a single-vessel reaction without isolation of the intermediates.

The process is illustrated by the following reaction diagram, the starting material being 1-aminoanthraquinone and the propene derivative methacrylonitrile:

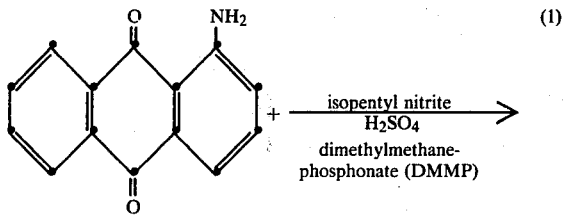

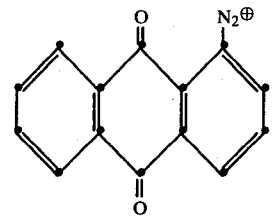

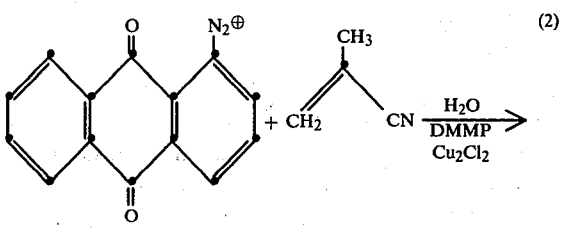

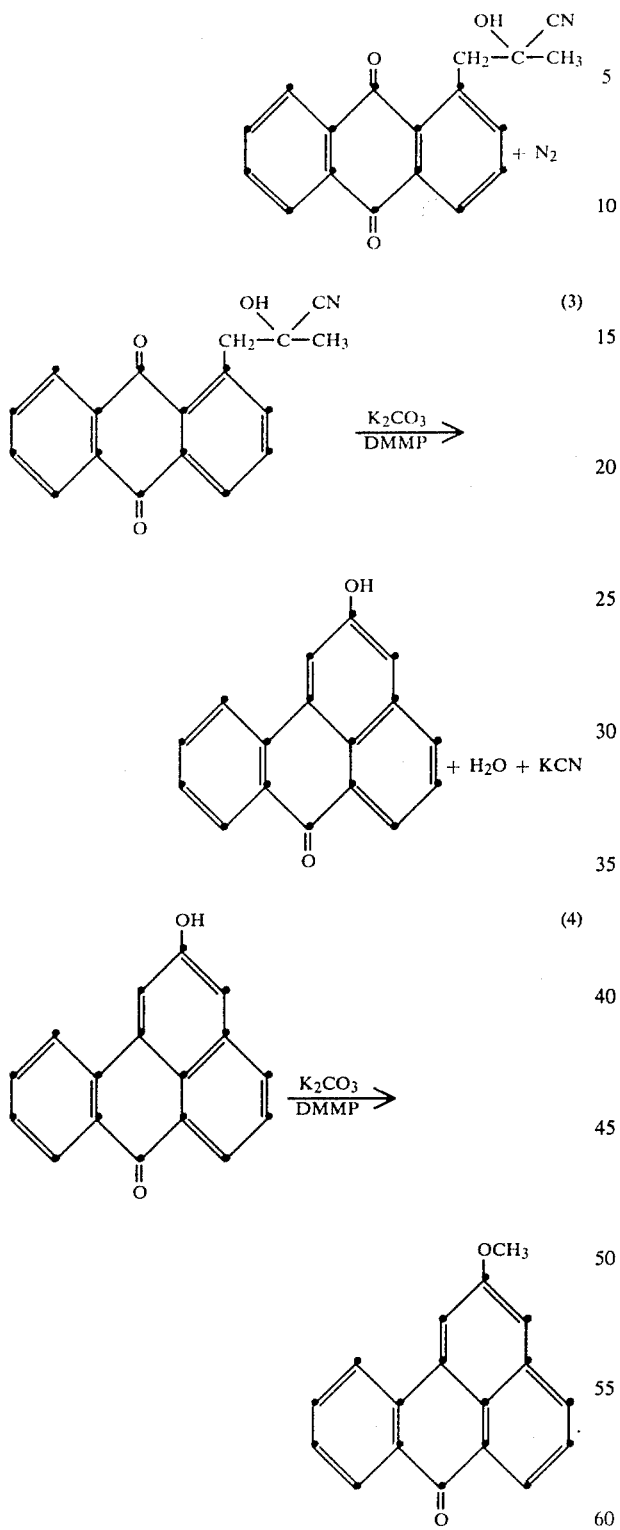

The reaction medium employed are dimethylalkanephosphonate, in which the alkane group has 1 to 4 C atoms, especially 1 or 2 C atoms, and particularly the dimethylmethanephosphonate of the formula

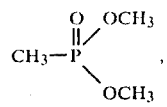

abbreviated to DMMP.

As diazotising agents are used nitrous acid esters, in particular those of primary or secondary alcohols having 1 to 10 carbon atoms. Examples of esters of this kind are the liquid nitrites of isopropyl, butyl, pentyl, isopentyl, heptyl and decyl alcohol, as well as benzyl alcohol, each having a boiling point above 50° C.; there are advantageously used the esters of alcohols having 1 to 5 carbon atoms, for example nitrites of methyl, ethyl, propyl-, isopropyl-, isobutyl- or isopentyl alcohol, which are gaseous or liquid. The esters can be added as such to the reaction mixture or after being dissolved in a solvent, for example in the same solvent as that in which the reaction is performed; the low-boiling esters can also be introduced in the gaseous state. Isopentyl nitrite or methyl nitrite is preferably used. Diazotisation can however also be carried out with for example nitrosyl chloride or nitrosylsulfuric acid. In this case however the resulting diazonium salt is advantageously isolated as an intermediate, the further reaction sequence, starting with diazonium salt, being performed as a single-vessel reaction according to the present invention.

In the second reaction step (Meerwein reaction), there are preferably used those propene derivatives of the formula

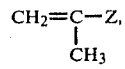

in which Z is a CN radical or the acetate group, that is to say, methacrylonitrile or isopropenyl acetate.

The following may be mentioned as starting materials for producing the methoxybenzanthrones according to the present invention: 4-hydroxy-1-aminoanthraquinone, 5-hydroxy-1-aminoanthraquinone, 5-methoxy-1-aminoanthraquinone, 5-chloro-1-aminoanthraquinone, 6,7-dichloro-1-aminoanthraquinone and 5-benzoamido-1-aminoanthraquinone, especially however unsubstituted 1-aminoanthraquinone.

The diazotisation reaction is performed at a temperature somewhat higher than that at which customary diazotisation reactions are carried out; the higher temperature is namely in the range of about 30°–80° C.

The reaction of the 1-anthraquinone-1-diazonium salt with the propene derivative (Meerwein reaction) is performed at a temperature of between 20° and 100° C., preferably simultaneously with diazotisation, so that the diazonium salt is always present only in small amounts.

The subsequent step of cyclisation by reaction of a base, preferably an alkali carbonate, is performed at temperatures of between 30° and 150° C., preferably between 70° and 140° C.

The last step of methylation is performed finally at 100°–150° C., in part simultaneously with cyclisation.

The proportions of the employed reagents correspond at least to the stoichiometrically required amounts. In the case of the propene derivative, it is advantageous to use an excess of 1–5 mols per mol of 1-aminoanthraquinone.

The copper-(I) chloride is applied in catalytic amounts of the order of only 0.003 to 0.1 mol, relative to 1 mol of anthraquinone-1-diazonium salt.

The dimethylalkanephosphonate employed as reaction medium and methylation agent is used, relative to the starting compound, in a weight ratio of 2:1 to 10:1.

In an advantageous embodiment, the process according to the invention is performed in the following manner:

Half of the employed 1-aminoanthraquinone is placed into the three-fold amount of dimethylmethanephosphonate, and sulfuric acid (96%) is added. After the addition of methacrylonitrile, the temperature is raised to 60°–70° C., and Cu(I) chloride as well as approximately half the isopentyl nitrite are added dropwise in the course of 10–60 minutes, with the evolution of nitrogen occurring immediately. There are then added the second half of the 1-aminoanthraquinone and the 1.5-fold amount by weight of dimethylmethanephosphonate, as well as again Cu(I) chloride. The second half of the isopentyl nitrite is now added dropwise, and stirring is maintained for about 10–30 minutes. By virtue of this procedure, steps 1 and 2 of the given reaction scheme occur practically simultaneously. After the evolution of nitrogen has ended, an alkali carbonate, preferably potassium carbonate, is added; the reaction mixture is heated to about 140° C. and is held, with stirring, for ¼–1 hour at 140°–150° C., in the course of which the steps 3 and 4 occur partially simultaneously. During heating up, excess methacrylonitrile and the formed isopentyl alcohol distil off, and $CO_2$ is evolved. After completion of the reaction, the temperature is lowered to 100°–130° C. and, by inoculation with pure 2-methoxybenzanthrone and further cooling to 15° C., the formed product is crystallised out. The product is filtered off, washed firstly with DMMP, then with water and optionally dried.

By virtue of the application of dimethylalkanephosphonates, and particularly of dimethylmethanephosphonate, as the reaction medium, which at the same time is the methylation agent, the process according to the invention for producing methoxybenzanthrones constitutes, compared with the relevant processes of the prior art, a simplification of the reaction procedure. By use of the novel process, 2-methoxybenzanthrones are obtainable in a single-vessel reaction without isolation of intermediates, the diazonium salt occurring as intermediate being present at all times only in small amounts.

There are obtained higher product and space-time yields compared with those of known processes; and since moreover the product is only very slightly soluble in the applied reaction medium (1% at room temperature), the isolation of the product is very simple.

The Examples which follow further illustrate the novel process according to the invention. The temperatures are given in degrees Centigrade.

EXAMPLE 1

33.8 g of 1-aminoanthraquinone (99%) are placed into 100 ml of dimethylmethanephosphonate, and 15.3 g of sulfuric acid (96%) are added in the course of 5 minutes with stirring. After the addition of 101 ml of methacrylonitrile (99%) and heating of the mixture to 65°, there is added 0.1 g of Cu(I)-chloride, followed by the dropwise addition at 68°–70° within 15 minutes of 18.5 g of isopentyl nitrite (90%), in consequence of which the evolution of nitrogen commences immediately. There are subsequently added a further 33.8 g of 1-aminoanthraquinone (99%), 50 ml of dimethylmethanephosphonate as well as 0.1 g of Cu(I)-chloride. At 68°–72° are then added 22.2 g of isopentyl nitrite within 15 minutes, and stirring is maintained at 70°–73° for 15 minutes. After the evolution of gas has ended, 66.3 of anhydrous, finely ground potassium carbonate are introduced within 10 minutes; the mixture is then heated in the course of 50 minutes to 140°, and is held for 1 hour at 140°–145°, during which $CO_2$ is liberated, and a total of about 105 ml of a mixture mainly of methacrylonitrile and isopentyl alcohol distil off. The reaction mixture is allowed to cool with stirring, and inoculation is performed at 120° with 0.5 g of 2-methoxybenzanthrone. The mixture is subsequently cooled from 60° by means of ice-water to 15°, and stirred for a further 30 minutes at 15°. It is squeezed on a glass frit under nitrogen; the residue is washed with 100 ml of dimethylmethanephosphonate, and afterwards washed neutral with water. After drying at 80° in vacuo and removal of 0.5 g of seed crystals, the yield is 58.5 g of 2-methoxybenzanthrone having a content of 98%, corresponding to 56.7 g of 2-methoxybenzanthrone (100%)=73.5% of theory, calculated relative to employed 1-aminoanthraquinone; melting point: 168°–169° C.: sintered: >160° C.

EXAMPLE 2

67.6 g of 1-aminoanthraquinone are added, within 1 hour, to 108 g of nitrosylsulfuric acid (38.8%) and 36.8 g of sulfuric acid (98%) in a 200 ml flask, the temperature not being allowed to exceed 50°. The solution is stirred at 45°–50° for a further 30 minutes, and is then poured with vigorous stirring onto 200 g of ice. The beige-coloured slurry is filtered under suction, well squeezed, and afterwards washed with 100 ml of ice-water (moist weight about 150–160 g).

The moist anthraquinone-1-diazonium hydrosulfate is introduced into 150 ml of dimethylmethanephosphonate in a 500 ml flask, and 80.8 g of methacrylonitrile are added. There are then added at 50°–53° in the course of 1 hour, with stirring, a total of 1.3 g of copper(I) chloride in portions, as a result of which nitrogen and hydrogen cyanide are evolved. After subsequent stirring for 15 minutes at 50°–55°, the apparatus is evacuated down to 60 mm Hg, and excess methacrylonitrile is distilled off at 50°–55°. After opening to the air, there are introduced 124.4 g of ground potassium carbonate within 15 minutes, with the evolution of $CO_2$-gas commencing. When the addition has ended, the temperature is 75°, and a thick paste forms. The oil bath is heated within 50 minutes to 160°, and when the reaction mixture has reached 140°, stirring is maintained for 30 minutes at 140°–5°. The mixture is allowed to cool, and at 100° are slowly added dropwise 150 ml of water. The cooled mixture is filtered off and washed neutral with about 600 ml of water. After drying at 80° in vacuo, the yield is 77–80 g of crude 2-methoxybenzanthrone having a content of 77–80%, corresponding to a yield of pure 2-methoxybenzanthrone of 77–80% of theory (calculated relative to the employed 1-aminoanthraquinone).

PURIFICATION

The dried crude product is subsequently suspended in 50 ml of dimethylmethanephosphonate and stirring is maintained for 30 minutes. The suspension is filtered off, washed with 50 ml of dimethylmethanephosphonate and afterwards with about 150 ml of water, and then dried to vacuo to thus obtain 56–59 g of 2-methoxybenzanthrone, corresponding to 71.5–75.5% of theory (calculated relative to employed 1-aminoanthraquinone), having a content of 96–99%.

EXAMPLE 3

11.4 g of 1-aminoanthraquinone (98%) are suspended in 20 ml of dimethylmethanephosphonate (DMMP), and 8.4 ml of isopentyl nitrite (90%) are added. There are then added dropwise at 20°–30°, within 1 hour, 2.92 ml of sulfuric acid (96%). The mixture is heated to 55°, and stirred for ½ hour at this temperature. After the addition of 21 ml of methacrylonitrile, a total of 150 mg of Cu(I) chloride is introduced portionwise at 55°–60° within 20 minutes, as a result of which the evolution of nitrogen commences. Excess methacrylonitrile is subsequently distilled off under a vacuum of 40 mm Hg, whereupon 30 ml of dimethylmethanephosphonate and 20.7 g of potassium carbonate are added. The reaction mixture is heated within 15 minutes to 140°, and stirred for 1 hour at 140°–145°; it is then allowed to cool, and 100 ml of water are added at 100°. The mixture is filtered under suction at room temperature, and washed neutral with water. The dried crude 2-methoxybenzanthrone (13.2 g) is suspended in 20 ml of DMMP, the suspension is stirred for 30 minutes, filtered under suction, and the residue is washed with 20 ml of DMMP and subsequently with water. The yield after drying at 60° in vacuo is 10.1 g of 2-methoxybenzanthrone having a content of 86.5%, corresponding to 8.74 g of 2-methoxybenzanthrone (100% = 67.3% of theory, calculated relative to the amount of 1-aminoanthraquinone used).

EXAMPLE 4

4.2 g of nitrosyl chloride are introduced, below the surface, into 50 ml of dimethylmethanephosphonate, and into the yellowish-brown solution at 20° are fed, within 1 hour, 11.4 g of 1-aminoanthraquinone. The beige-coloured suspension is stirred for 1 hour at 20°–25° and for ¾ hour at 50°. There are then added 21 ml of methacrylonitrile, and at 50°–55° are introduced, within 45 minutes, 8 portions each of 50 mg of $Cu_2Cl_2$, making a total of 0.4 g, in consequence of which the evolution of nitrogen commences. After the evolution of gas has finished, the reaction vessel is evacuated down to a vacuum of 60 mm Hg, and excess methacrylonitrile is distilled off at 50°–55°. After release of the vacuum, 15 ml of dimethylmethanephosphonate and 17.3 g of potassium carbonate are added at 65°. The mixture is heated within 30 minutes to 140°, and the escape of $CO_2$- and HCN-gas then occurs. After subsequent stirring at 140°–145° for 20 minutes, the mixture is allowed to cool, and at 100° are slowly added dropwise 75 ml of water. The cooled mixture is filtered, and washed neutral with about 100 ml of water. The yield after drying at 80° in vacuo is 14.3 g of crude 2-methoxybenzanthrone.

EXAMPLE 5

22.5 g of 1-aminoanthraquinone are introduced, within 1 hour, into 36 g of nitrosylsulfuric acid (38.8%) and 12.3 g of sulfuric acid (98%), the temperature not being allowed to exceed 50°. The solution is stirred at 45°–50° for 30 minutes, and is then poured with vigorous stirring onto 70 g of ice. The beige-coloured slurry is filtered under suction, well squeezed out, and washed with 35 ml of ice-water. The moist anthraquinone-1-diazonium hydrosulfate is suspended in 50 ml of dimethylmethanephosphonate. After the addition of 22.2 ml of isopropenyl acetate, there is added at 25°–35° within 1½ hours, at intervals of 9 minutes, a total of 11 portions each of 0.1 g of Cu(I)-chloride, whereby nitrogen is liberated. The temperature is subsequently raised to 50°–55° and, with slow evacuation to a final vacuum of 13 mm Hg and a temperature of 70°, a total of about 20 ml of distillate is obtained. After release of the vacuum, 55.2 g of potassium carbonate are introduced. The mixture is heated within 1 hour to 140°, and held for 45 minutes at 140°–145°, in the course of which $CO_2$ escapes and in all a further 10 ml of distillate are obtained. The mixture is allowed to cool, and at 100° are added dropwise 50 ml of water. After cooling to room temperature, the crude product is filtered off, washed neutral with water, and dried at 60° in vacuo. The dry crude product (~25.4 g) is introduced into 15 ml of dimethylmethanephosphonate, and stirring is maintained for 30 minutes at room temperature. After filtration, washing of the residue with 15 ml of dimethylmethanephosphonate and subsequently with water, the yield is 21.3 g of 2-methoxybenzanthrone having a content of 90%, which corresponds to 19.1 g of pure 2-methoxybenzanthrone = 73.6% of theory, calculated relative to the amount of 1-aminoanthraquinone used.

EXAMPLE 6

A mixture of 100 ml of dimethylmethanephosphonate, 83.3 g of methacrylonitrile (99%) and 33.8 g of 1-aminoanthraquinone (99%) are placed into a 500 ml flask, and 24.6 g of 60% sulfuric acid are added dropwise with stirring. The dark-red suspension is heated to 65° and, after the addition of 0.1 g of copper(I) chloride, there is introduced at 65°–68° under the surface, within 40 minutes, methyl nitrite (produced by the dropwise addition of 19.3 g of 40% sulfuric acid to a solution of 24 g of sodium nitrite in 12 g of methanol and 10 ml of water). The evolution of nitrogen indicates the instantaneous commencement of the reaction. After subsequent stirring for 10 minutes, there are added to the reaction mixture a further 33.7 g of 1-aminoanthraquinone together with 0.1 g of copper(I) chloride, and at 68°–71° methyl nitrite is again introduced within 50 minutes. After the evolution of nitrogen has finished, there are distilled off from the reaction mixture, at a temperature of 80° and a pressure of 80 mbar, about 78 g of a mixture of methanol and methacrylonitrile. At 75° are subsequently added 50 ml of dimethylmethanephosphonate, and then 27.9 g of potassium carbonate are introduced, whereupon carbon dioxide escapes. The reaction mixture is afterwards heated to 100°, and a further 39 g of potassium carbonate are added in the course of 15 minutes, the internal temperature rising as a result to 130°. Stirring is maintained finally for 30 minutes at 140°, and the mixture is then allowed to cool to 15°. An addition of 0.5 g of methoxybenzanthrone (seed crystals) is made at a temperature of 120°. The reaction mixture is stirred at 15° for 1 hour; the dark-brown crystal mass is then squeezed out on a glass frit, and is washed with 100 ml of dimethylmethanephosphonate. A further 500 ml of water is used to wash the residue until it is salt-free and neutral, and it is then dried by suction; the resulting product is subsequently dried at 80° in vacuo to thus obtain 55–59 g of 2-methoxybenzanthrone having a degree of purity of 96–99%; yield 70–73%; melting point 168°–169°.

What is claimed is:

1. A process for producing a 2-methoxybenzanthrone, starting with 1-aminoanthraquinone of the formula I

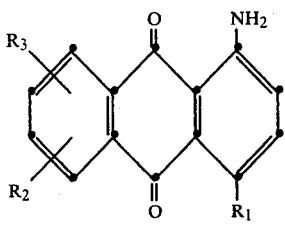

or the corresponding anthraquinone-1-diazonium salt, wherein $R_1$, $R_2$ and $R_3$ independently of one another are each hydrogen or chlorine, or the hydroxyl, methoxy or benzamido group, in which process the starting compound is reacted to give the anthraquinone-1-diazonium salt, this in its turn is reacted in a Meerwein reaction with a propene derivative of the formula

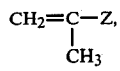

wherein Z is an electron-attracting substituent, and the reaction product is then cyclised in an alkaline reaction mixture to obtain 2-hydroxybenzanthrone, the hydroxyl group of which is methylated, by reaction with the reaction medium, to yield 2-methoxybenzanthrone, the said process being characterised in that it is performed, without isolation of the intermediates, in a dimethylalkanephosphonate, of which the alkane radical has 1–4 C atoms.

2. A process according to claim 1, wherein the reaction medium used is dimethylmethanephosphonate.

3. A process according to claim 1, wherein the diazotisation and the Meerwein reaction are performed simultaneously.

4. A process according to claim 1, wherein the starting compound used is unsubstituted 1-aminoanthraquinone.

5. A process according to claim 1, wherein there are used for diazotisation the nitrous acid esters of alcohols having 1–5 C atoms, or nitrosyl chloride or nitrosylsulfuric acid.

6. A process according to claim 1, wherein the anthraquinone-1-diazonium salt is reacted with a propene derivative of the formula

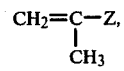

in which Z is the cyano group or an acetate radical.

7. A process according to claim 6, wherein methacrylonitrile is used.

8. A process according to claim 1, wherein the cyclisation reaction is performed by means of alkali carbonates.

9. A process according to claim 8, wherein anhydrous potassium carbonate is used.

10. A process according to claim 1, wherein diazotisation is performed at a temperature of between 30° and 80° C.; the Meerwein reaction at a temperature of between 20° and 100° C.; and cyclisation as well as methylation at a temperature of between 30° and 150° C.

11. A process according to claim 1, wherein the dimethylalkanephosphonate is used in a weight ratio of 2:1 to 10:1, relative to the 1-aminoanthraquinone.

* * * * *